United States Patent [19]

Schmidt

[11] 4,271,196

[45] Jun. 2, 1981

[54] PHARMACEUTICAL COMPOSITIONS FOR PARENTERAL OR LOCAL ADMINISTRATION

[75] Inventor: Dieter Schmidt, Basel, Switzerland

[73] Assignee: Hoffmann-La Roche Inc., Nutley, N.J.

[21] Appl. No.: 94,813

[22] Filed: Nov. 16, 1979

[30] Foreign Application Priority Data

Nov. 21, 1978 [CH] Switzerland ...................... 11921/78

[51] Int. Cl.³ .................... A61K 31/685; A61K 47/00

[52] U.S. Cl. .................................... 424/358; 424/199; 424/236; 424/244; 424/252; 424/255; 424/263; 424/284; 424/331; 424/344

[58] Field of Search ................................ 424/199, 358

Primary Examiner—Stanley J. Friedman
Attorney, Agent, or Firm—Jon S. Saxe; George M. Gould; William H. Epstein

[57] ABSTRACT

Colloidal aqueous vehicles, useful for the solubilization of insoluble or slightly soluble medicaments and suitable for parenteral or local administration, are disclosed. The vehicles contain, in addition to the medicaments, pharmaceutical adjuvants and a micelle-forming agent comprising short-chain lecithin and a non-hemolytic lipid.

7 Claims, No Drawings

PHARMACEUTICAL COMPOSITIONS FOR PARENTERAL OR LOCAL ADMINISTRATION

SUMMARY OF THE INVENTION

The present invention is directed to colloidal aqueous vehicles suitable for the parenteral or local administration of medicaments which are insoluble or only slightly soluble in water and to pharmaceutical compositions incorporating such vehicles. These pharmaceutical compositions comprise pharmaceutical adjuvants, one or more medicaments and, as the micelle forming agent, a short-chain lecitin and a non-hemolytic lipid.

BACKGROUND OF THE INVENTION

Heretofore, vehicles for rendering insoluble or sparingly soluble medicaments suitable for parenteral administration used, generally, one or a mixture of synthetic solubilizing agents such as propylene glycol, polyethylene glycols, various emulsifying agents such as those marketed under the tradenames Cremophor EL, Tweens and Pluronics. The latter group of solubilizing agents functions by the formation of a colloidal system (micelles). The synthetic solubilizing agents including the above-mentioned micelle forming agents can be disadvantageous in that, upon parenteral administration, they may cause side effects such as allergic reactions, anaphylactic shock, hemolysis and pyrogenic action.

In addition to the synthetic micelle-forming agents discussed above, there are natural micelle forming agents such as cholic acid and various derivatives thereof. These natural micelle forming agents are, however, ionic and, therefore, strongly lytic. They produce hemolysis and have accordingly not previously been considered for the preparation of compositions for parenteral administration.

U.S. Pat. No. 4,158,707 discloses that the disadvantageous lytic action of the cholic acid derivatives can be eliminated or substantially reduced by combining the cholic acid derivatives with certain pharmaceutically acceptable lipoids, e.g., phorphatidyl-cholines, glycerin ether phosphatides and phosphatidylethanolamines.

In addition, DOS No. 2,730,570 discloses aqueous solutions of insoluble or sparingly soluble medicaments, which are suitable for parenteral administration, wherein the micelle formers are gallic acid derivatives. The gallic acid derivatives, however, have a cholectic activity which is undesirable.

DETAILED DESCRIPTION OF THE INVENTION

This invention is directed to colloidal aqueous vehicles suitable for parenteral or local administration of insoluble or sparingly soluble medicaments, i.e., pharmaceutically active ingredients, to processes for preparing such vehicles and pharmaceutical compositions comprising such vehicles.

The colloidal aqueous vehicle utilizes, as the micelle forming agent, a combination of a short-chain lecithin and a non-hemolytic lipid. A non-hemolytic lipid is a lipid which does not have hemolytic activity.

Lecithins are mixed esters of glycerol and choline with fatty acids and phosphoric acid having the formula

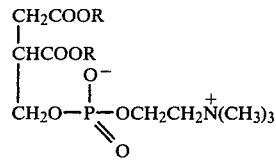

wherein R is a fatty acid radical.

A short-chain lecithin is one which contains lower acyl groups. "Lower acyl" is defined as acyl, particularly alkanoyl containing up to 7 carbon atoms.

These short-chains lecithins dissolve in water to give clear micelles and they are also capable of solubilizing small amounts of insoluble or sparingly soluble pharmaceutically active compounds. In many cases, the amount of pharmaceutically active ingredient solubilized is too small to be pharmaceutically effective. Further, the short-chain lecithin micelles, including pure dihexanoyl lecithin micelles, can still have hemolytic activity.

To overcome both the minimal solubilizing effect and the hemolytic activity of short-chain lecithins, the colloidal aqueous vehicles of this invention use a micelle-forming agent which is a combination of a short-chain lecithin, i.e., dihexanoyl lecithin, and a non-hemolytic lipid.

Stable, mixed micelles, which are non-hemolytic and capable of solubilizing pharmaceutically effective amounts of insoluble or sparingly soluble pharmaceutically active ingredients, are prepared from the combination of a short-chain lecithin, i.e., dihexanoyl lecithin, with a lipid and, in particular, with a long-chain lecithin.

Heretofore it was believed that different long-chain lecithins could be satisfactorily mixed only when they differed as little as possible in the lengths of their carbon chains. It has now been found that long-chain lecithins such as natural egg lecithin or soya lecithin combine with a short-chain lecithin such as dihexanoyl lecithin to yield a micelle-forming agent which is non-hemolytic and capable of solubilizing insoluble or sparingly soluble pharmaceuticals.

Preferred non-hemolytic lipids are phosphatides or glycerides. Examples of phosphatides include egg lecithin, soya lecithin, dipalmitoyl lecithin, dimyristoyl lecithin and phosphatidyl inositol. Examples of glycerides are monoolein and monolinolein. Especially preferred non-hemolytic lipids are egg lecithin and soya lecithin.

The ratio of non-hemolytic lipid to short-chain lecithin can vary within a rather wide range. The lower limit of the non-hemolytic lipid is the amount necessary to suppress the hemolytic activity which is inherent in the short-chain lecithin, i.e., dihexanoyl lecithin. The upper limit for the non-hemolytic lipid is determined by the solubilizing capabilities of the dihexanoyl lecithin. A mole ratio of non-hemolytic lipid to dihexanoyl lecithin in the range of 1:3 to 1:1 is preferred with a ratio of 1:2 to 1:1 especially preferred.

The amount of the combination of the micelle-forming agent in the compositions of this invention can also vary within wide limits. It is preferred, however, that the amount of the combination in the final compositions is between from about 50 mg/ml to about 200 mg/ml.

The colloidal aqueous compositions of this invention which contain, as the micelle-forming agent, a combination of dihexanoyl lecithin and a non-hemolytic lipid can also contain one or more pharmaceutically active ingredients which are insoluble or only slightly soluble in water and, optionally, pharmaceutically active ingredients which are soluble in water as well as pharmaceutical adjuvants.

Pharmaceutically active ingredients which are insoluble or only slightly soluble in water and which are suitable for use in the compositions of this invention include, in particular, benzodiazepines and fat-soluble vitamins. Neuroleptics, antidepressants, anti-infective agents and steroids which are water-insoluble or only slightly soluble can also be used in the compositions of this invention.

Examples of benzodiazepines are diazepam, clonazepam, flunitrazepam, medazepam and bromazepam. Diazepam is especially preferred.

Examples of fat-soluble vitamins are vitamins A, D, E and K and derivatives thereof. Vitamin E acetate and vitamin $K_1$ are preferred.

Examples of pharmaceutical active substances which are soluble in water and which can be used in the compositions of this invention are water-soluble vitamins such as vitamin $B_1$, vitamin $B_6$, vitamin $B_{12}$ and mixtures of two or more of these vitamins.

Examples of pharmaceutical adjuvants include antioxidants such as sodium hydrogen sulphite, sodium pyrosulphite or vitamin E acetate.

Other pharmaceutical adjuvants suitable for use in the colloidal aqueous compositions of this invention include isotonising additives such as sodium chloride solution, glucose solution, Tris buffer, phosphate buffer, citrate buffer, glycine buffer, citrate-phosphate mixed buffer and the like.

A water-soluble, non-toxic organic solvent such as ethanol can also be used as a pharmaceutical adjuvant in the compositions of this invention. Up to about 6% of ethanol can be present in a composition to be used for parenteral administration and up to about 40% of ethanol can be present in a composition to be used for local administration.

In the compositions of the instant invention, part of the dihexanoyl lecithin can be replaced by more than the equivalent amount of dibutyryl lecithin.

The colloidal aqueous compositions of this invention containing pharmaceutically active ingredients which are only slightly soluble or insoluble in water are suitable for parenteral or local administration. The amount of such pharmaceutically active ingredients in the colloidal aqueous compositions can vary within wide limits and can range, for example, from about 0.1 mg/ml to about 20 mg/ml of solution.

The osmotic pressure of injection or infusion solutions can vary within certain limits and should, advantageously, approximate that of blood.

The colloidal aqueous compositions of this invention can be prepared by simple admixture of the individual components. This procedure is especially applicable in the case of a low molar ratio of non-hemolytic lipid to dihexanoyl lecithin (e.g., a ratio range of 1:3 to 1:2). The time required to obtain a homogeneous mixture can be shortened by warming.

A preferred method for the preparation of the aqueous colloidal compositions of this invention comprises dissolving dihexanoyl lecithin, the non-hemolytic lipid and, as desired, one or more pharmaceutically active ingredients which are insoluble or only slightly soluble in water in a suitable organic solvent in which the components are sufficiently soluble. The organic solvent would then be removed by evaporation and water or buffer solution would subsequently be added.

In an especially preferred embodiment for the preparation of the aqueous colloidal compositions, dihexanoyl lecithin, up to about one molar equivalent of non-hemolytic lipid, from about 100 to about 200 molar equivalents of water and, if desired, one or more pharmaceutically active ingredients which are insoluble or only slightly soluble in water are stirred vigorously until the mixture is homogeneous. Then, additional water or buffer solution is added until the desired dilution or concentration is achieved.

The time required to form the homogeneous mixture by stirring can generally be reduced by warming the mixture for a short period or by adding an organic solvent, i.e., ethanol.

When the ratio of non-hemolytic lipid to dihexanoyl lecithin is about equimolar (e.g. between 0.9:1 and 1:1), the compositions are prepared by dissolving both the dihexanoyl lecithin and the non-hemolytic lipid in a suitable organic solvent (e.g. an alcohol such as ethanol), removing the solvent by evaporation and adding from about 100 to 200 mols of water per mol of dihexanoyl lecithin. This phase is homogenized while warming to about 80° C. within about 15 minutes. Water or buffer solution is then added until the desired concentration or dilution is achieved.

The aqueous, colloidal vehicles can also be prepared, as described earlier, prior to the introduction into the compositions of the pharmaceutical active ingredients which are insoluble or only slightly soluble in water. This procedure is especially suitable for the solubilization of benzodiazepines.

The following Examples illustrate this invention.

EXAMPLE 1

1.36 mmol (620 mg) of dihexanoyl lecithin and 1.22 mmol (939 mg) of egg lecithin were dissolved in about 30 ml of ethanol. The egg lecithin was isolated according to Singleton et al., J. Amer. Oil. Chem. Soc. 42 53 (1965). The ethanol was removed by rapid evaporation in vacuo at about 30° C. to produce a film. This film was dissolved with 1/15 M phosphate buffer solution to form 10 ml of a clear aqueous composition.

EXAMPLE 2

1 mmol (453 mg) of dihexanoyl lecithin and 500 µmol (455 mg) of soya lecithin were admixed well with 2 ml of 1/15 M phosphate buffer (pH 7) in a vortex. After standing at room temperature for several hours, a clear viscous phase formed which was dissolved with 1/15 M phosphate buffer solution to give 10 ml of an aqueous composition.

EXAMPLE 3

The procedure of Example 2 was repeated, but the viscous phase was formed by warming the mixture to about 80° C. for about 15 minutes.

EXAMPLE 4

1 mmol (453 mg) of dihexanoyl lecithin and 500 µmol (445 mg) of soya lecithin were mixed with 10 ml of 1/15 M phosphate buffer solution. The mixture was stirred at room temperature for about 18 hours to form a clear aqueous composition.

EXAMPLE 5

The procedure of Example 4 was repeated, but the solubilization was completed by stirring at about 80° C. for about 1 hour.

EXAMPLE 6

1 mmol (453 mg) of dihexanoyl lecithin and 1 mmol (890 mg) of egg lecithin were dissolved in about 30 ml of ethanol. The ethanol was removed by rapid evaporation in vacuo at about 30° C. to produce a film. This film was admixed well with about 3 ml of 1/15 M phosphate buffer solution. After standing at room temperature for about 1 hour, a clear viscous phase formed which was diluted with additional phosphate buffer solution to a final volume of 10 ml.

EXAMPLE 7

1.36 mmol (620 mg) of dihexanoyl lecithin and 1.22 mmol (939 mg) of egg lecithin were dissolved, together with 33 mg of diazepam, in 30 ml of ethanol. The ethanol was removed by rapid evaporation in vacuo at about 30° C. to produce a film. This film was dissolved with 1/15 M phosphate buffer solution to form 10 ml of a clear composition.

EXAMPLE 8

The procedure of Example 7 was repeated with the modification that the diazepam was added to the vehicle at the end.

EXAMPLE 9

650 μmol (295 mg) of dihexanoyl lecithin and 400 μmol (308 mg) of egg lecithin were dissolved, together with 100 mg of vitamin $K_1$, in 30 ml of ethanol. The ethanol was removed by rapid evaporation in vacuo at about 30° C. to form a film. This film was mixed with 1 ml of 1/15 M phosphate buffer solution and, after warming at about 80° C. for 2 hours, a clear yellow phase formed. This clear yellow phase was dissolved with further phosphate buffer solution to form 10 ml of a clear composition.

EXAMPLE 10

1 mmol (453 mg) of dihexanoyl lecithin, 500 μmol (445 mg) of soya lecithin and 25 mg of diazepam were admixed well with 2 ml of 1/15 M phosphate buffer solution (pH 7) and left at room temperature for several hours until a clear viscous phase formed. This clear viscous phase was dissolved with further phosphate buffer solution to form 10 ml of a clear composition.

EXAMPLE 11

1 mmol (453 mg) of dihexanoyl lecithin, 500 μmol (445 mg) of soya lecithin and 100 mg of vitamin $K_1$ were admixed well with 2 ml of 1/15 M phosphate buffer solution (pH 7). The admixture was then heated at about 80° C. for 2 hours to form a clear, somewhat viscous phase. This phase was diluted with additional phosphate buffer to form 10 ml of an aqueous composition.

EXAMPLE 12

The procedure of Example 11 was repeated with 100 mg of vitamin E acetate used in place of the vitamin $K_1$.

EXAMPLE 13

5.6 mmol (2.54 g) of dihexanoyl lecithin, 4.2 mmol (3.23 g) of egg lecithin and 115.5 mg of diazepam were dissolved in about 100 ml of ethanol. The ethanol was removed by rapid evaporation in vacuo at about 30° C. to form a film. This film was dissolved with 1/15 M phosphate buffer solution, previously saturated with nitrogen, to form 35 ml of a clear aqueous composition. This aqueous composition was subsequently filtered sterile under laminar flow conditions and filled into 3 ml ampoules containing nitrogen. The ampoules were then sealed. During the entire procedure, air contact was avoided to obtain oxygen-free solutions in the sealed ampoules.

EXAMPLE 14

2.1 mmol (951 mg) of dihexanoyl lecithin, 1.4 mmol (1078 mg) of egg lecithin and 350 mg of vitamin $K_1$ were dissolved in about 100 ml of ethanol. The ethanol was removed by rapid evaporation in vacuo at about 30° C. to form a film. This film was admixed with about 3.5 ml of 1/15 M phosphate buffer solution and about 0.7 ml of ethanol. After standing at room temperature for 4 days, a clear, viscous phase formed. This phase was diluted with additional 1/15 M phosphate buffer solution, previously saturated with nitrogen, to form 35 ml of a clear, yellow aqueous composition. This aqueous composition was filtered sterile under laminar flow conditions and filled into 1 ml ampoules containing nitrogen. During the entire procedure contact with air was avoided in order to obtain oxygen-free solutions in the ampoules.

EXAMPLE 15

3.6 mmol (1430 mg) of dibutanoyl lecithin, 0.6 mmol (272 mg) of dihexanoyl lecithin, 1.2 mmol (924 mg) of egg lecithin and 33 mg of diazepam were dissolved in 30 ml of ethanol. The ethanol was removed by rapid evaporation in vacuo at about 30° C. to form a film. This film was dissolved with 1/15 M phosphate buffer solution to form 10 ml of a clear composition.

EXAMPLE 16

1.0 mmol (453 mg) of dihexanoyl lecithin, 1.5 mmol (1.335 g) of soya lecithin and 5 mg of 9-(4-methoxy-2,3,6-trimethylphenyl)-3,7-dimethyl-nona-2,4,6,8-tetraen-1-oic acid ethylamide were dissolved in 4 ml of ethanol. The resulting solution was then diluted slowly with stirring with 1/15 M phosphate buffer solution to a volume of 10 ml.

I claim:

1. An aqueous colloidal composition which comprises a combination of dihexanoyl lecithin and non-hemolytic lipid selected from the group consisting of egg lecithin, soya lecithin, dipalmitoyl lecithin, dimyristoly lecithin, phosphatidyl inositol, monoolein and monolinolein, wherein the concentration of the combination ranges from about 50 mg per ml to about 200 mg per ml of the aqueous colloidal composition and wherein the mole ratio of dihexanoyl lecithin to non-hemolytic lipid ranges from about 1:3 to about 1:1.

2. The composition of claim 1 wherein the non-hemolytic lipid is a phosphatide.

3. The composition of claim 2 wherein the phosphatide is egg lecithin.

4. The composition of claim 2 wherein the phosphatide is soya lecithin.

5. The composition of claim 2 wherein the phosphatide is dipalmitoyl lecithin.

6. The composition of claim 2 wherein the phosphatide is dimyristoyl lecithin.

7. The composition of claim 2 wherein the phospatide is phosphatidylinositol.

* * * * *